US008834919B2

(12) United States Patent
Weinberg et al.

(10) Patent No.: US 8,834,919 B2
(45) Date of Patent: *Sep. 16, 2014

(54) LIPID EMULSIONS IN THE TREATMENT OF SYSTEMIC POISONING

(76) Inventors: Guy Weinberg, Northbrook, IL (US); Paul Hertz, Skokie, IL (US)

( * ) Notice: Subject to any disclaimer, the term of this patent is extended or adjusted under 35 U.S.C. 154(b) by 1466 days.

This patent is subject to a terminal disclaimer.

(21) Appl. No.: 11/828,220

(22) Filed: Jul. 25, 2007

(65) Prior Publication Data

US 2008/0021411 A1 Jan. 24, 2008

Related U.S. Application Data

(63) Continuation-in-part of application No. 09/622,816, filed as application No. PCT/US99/03805 on Feb. 22, 1999, now Pat. No. 7,261,903.

(60) Provisional application No. 60/075,717, filed on Feb. 24, 1998.

(51) Int. Cl.
*A61K 9/127* (2006.01)
*A61K 9/107* (2006.01)

(52) U.S. Cl.
CPC .............. *A61K 9/107* (2013.01); *Y10S 514/937* (2013.01); *Y10S 514/938* (2013.01); *Y10S 514/943* (2013.01)
USPC ........... 424/450; 424/400; 514/937; 514/938; 514/943

(58) Field of Classification Search
CPC ............................. A61K 9/127; A61K 9/107
USPC ................... 424/450, 400; 514/937, 938, 943
See application file for complete search history.

(56) References Cited

U.S. PATENT DOCUMENTS

| 2,322,822 | A | | 6/1943 | Brown |
| 3,538,216 | A | | 11/1970 | Polin |
| 4,011,238 | A | * | 3/1977 | Fontanella et al. ........ 548/314.7 |
| 4,115,313 | A | | 9/1978 | Lyon et al. |
| 4,161,522 | A | | 7/1979 | Hamburger et al. |
| 4,183,918 | A | | 1/1980 | Asher et al. |
| 4,323,563 | A | | 4/1982 | Takami et al. |
| 4,623,334 | A | * | 11/1986 | Riddell .......................... 604/85 |
| 4,719,239 | A | | 1/1988 | Muller et al. |
| 4,784,845 | A | | 11/1988 | Desai et al. |
| 4,801,455 | A | | 1/1989 | List et al. |

(Continued)

FOREIGN PATENT DOCUMENTS

GB         2 050 799         1/1981

OTHER PUBLICATIONS

Cave et al. (2005), "Intralipid ameliorates thiopentone induced respiratory depression in rats: Investigative pilot study"; *Emergency Medicine Australasia* 17:180-183.

(Continued)

*Primary Examiner* — Gollamudi Kishore
(74) *Attorney, Agent, or Firm* — Lathrop & Gage LLP

(57) ABSTRACT

The present invention provides lipid emulsions and methods of intravenously administering lipid emulsions to treat systemic toxicity caused by foreign lipophilic and amphiphilic substances. In particular, methods are provided to treat cardiovascular impairment, such as cardiotoxicity, asystole and ischemia of the brain and heart, and neurological impairments, such as seizures and comas, caused by foreign lipophilic and amphiphilic substances, including cardiovascular impairment caused by local anesthetics, tricyclic antidepressants, sodium channel blockers, and calcium channel blockers.

9 Claims, 4 Drawing Sheets

Comparison of Time to Asystole in Rats Given Cocaine
Rate of Infusion: 5 mg/kg/min
P<0.003

(56) References Cited

U.S. PATENT DOCUMENTS

| | | | |
|---|---|---|---|
| 4,837,028 | A | 6/1989 | Allen et al. |
| 4,882,164 | A | 11/1989 | Ferro et al. |
| 4,954,239 | A * | 9/1990 | Mueller ................ 206/571 |
| 4,997,819 | A | 3/1991 | Yamaguchi et al. |
| 5,089,268 | A | 2/1992 | Katz |
| 5,139,023 | A | 8/1992 | Stanley et al. |
| 5,291,887 | A | 3/1994 | Stanley et al. |
| 5,389,373 | A | 2/1995 | Davis et al. |
| 5,438,041 | A | 8/1995 | Zheng et al. |
| 5,478,860 | A | 12/1995 | Wheeler et al. |
| 5,536,413 | A | 7/1996 | Bormann et al. |
| 5,569,649 | A | 10/1996 | Allison et al. |
| 5,610,294 | A * | 3/1997 | Lam et al. ................ 540/492 |
| 5,650,172 | A | 7/1997 | Matsuda et al. |
| 5,674,527 | A | 10/1997 | Inoue et al. |
| 6,139,871 | A | 10/2000 | Hope et al. |
| 6,383,490 | B1 * | 5/2002 | Wirsching et al. ......... 424/193.1 |
| 2007/0059346 | A1 * | 3/2007 | Maibach ................ 424/443 |

OTHER PUBLICATIONS

Goor and Goor (2003, "Letter to the editor: Has the silver bullet been found?" *Regional Anesthesia and Pain Medicine* 29(1):73-74.

Groban and Butterworth (2003), "Lipid reversal of bupivacaine toxicity: Has the silver bullet been identified?" *Regional Anesthesia and Pain medicine* 28(3):167-169.

Krieglstein et al. (1974), "Influence of emulsified fat on chlorpromazine availability in rat blood"; *Experientia* 30:924-926.

Weinberg (2003), "Lipid emulsion infusion rescues dogs from bupivacaine-induced cardiac toxicity"; *Regional Anesthesia and Pain Medicine* 28(3):198-202.

Weinberg (2003), "Letter to the editor: Reply to Drs. Goor, Groban, and Butterworth—Lipid Rescue: Caveats and Recommendations for the 'silver bullet'," *Regional Anesthesia and Pain Medicine* 29(1):74-75.

* cited by examiner

US 8,834,919 B2

LIPID EMULSIONS IN THE TREATMENT OF SYSTEMIC POISONING

CROSS-REFERENCE TO RELATED APPLICATIONS

This application is a continuation-in-part of pending U.S. application Ser. No. 09/622,816 filed on Jul. 17, 2001, which in turn claims priority to PCT/US99/03805 filed on Feb. 22, 1999, which in turn claims priority to U.S. Provisional Application 60/075,717 filed on Feb. 24, 1998, all of which are incorporated herein in their entirety to the extent not inconsistent herewith.

BACKGROUND OF THE INVENTION

This invention relates to lipid emulsion compositions and to methods of treating systemic toxicity by reducing the bioavailability of pharmaceuticals, poisons and other foreign agents present in the circulation by the intravenous infusion of a lipid emulsion composition. Of particular interest are methods and compositions to treat patients having adverse reactions to pharmaceutical drugs such as anesthetics or antidepressants. Anesthetics and similar substances can have severe adverse effects, particularly cardiovascular effects, if present in improper amounts. In cases of overdoses or allergic reactions, such effects can include heart failure and even death.

An emulsion is a collective of lipid or oil microparticles dispersed in water usually by the action of an emulsifying agent. Historically, emulsions have been widely used in the cosmetic and drug industries in connection with creams, depilatories, antiperspirants, deodorants, antiseptics and the like. Emulsion systems which include sugars, amino acids, vitamins, and electrolytes have also been utilized as a means of providing intravenous nutrition in order to maintain a patient's life when oral or nasal feeding is impossible or insufficient (see U.S. Pat. No. 5,674,527 to Inoue et al.). Another common use of emulsions is in parenteral drug delivery systems (see U.S. Pat. No. 3,538,216 to Polin et al.). These drug delivery systems feature hydrophobic medicinals suspended in an emulsion to be delivered to the patient in a sustained release manner. The lipid emulsion in this system consists of a thixotropic agent, a gelatinous-oil composition containing an ion-exchange agent, and water.

Also, edible but non-digestible emulsions have been used as traps for toxins present in the gastrointestinal (GI) tract as described in U.S. Pat. No. 4,183,918 to Asher et al. In this trap system, the emulsion is fed to a symptomatic patient wherein the toxins are removed by the action of the absorbent-containing emulsion passing through the GI tract. Key features of this system include the use of non-digestible oils as the exterior phase of the emulsion and the use of a reactant or adsorbent in the interior aqueous phase of the emulsion. Examples of exterior phase oils used in this system include highly refined hydrocarbon oils, mineral oils, and silicone oils, while preferred interior phase reactants and adsorbents include silica gel and carbon.

Other means of detoxifying the body include the delivery of liposomes containing active reagents to a patient. For example, an aqueous solution of the chelating agent EDTA was encapsulated by liposomes (synthetic membrane vesicles) and given to a patient undergoing chemotherapy in order to remove the radioactive metal plutonium from the patient's body. (Rahman et al., Science (1973) 180:300). Liposomes, in most cases, act by rupturing their membranes to release their inner contents. As such, liposomes have also been used to deliver drugs in a controlled release manner as described in U.S. Pat. No. 4,837,028 to Allen. However, liposomes are not readily permeable to extraneous toxic agents present in the body.

In light of the foregoing, a need remains for materials and methods to effectively decrease the bioavailability of foreign toxic substances in the bloodstream, especially lipophilic or amphiphilic agents such as antidepressants, anesthetics, alcohol, cocaine or others which require immediate intervention when present in dangerous amounts.

SUMMARY OF THE INVENTION

The present invention is directed to the use of an intravascular infusion of a lipid emulsion to treat severe systemic toxicity by reducing the bioavailability of foreign lipophilic or amphiphilic substances, or their metabolites, circulating in the bloodstream.

As used herein, toxicity and systemic toxicity refer to severe adverse effects a foreign substance has on the body, such as seizures, induction of coma, neurological damage and cardiovascular impairment, which includes but is not limited to low blood pressure (hypotension), ischemia, cardiac arrhythmia, cardiotoxicity, cardiovascular collapse, cardiac arrest, heart failure and asystole. Neurological impairments and symptoms, such as obtundation, agitation, coma and seizures, are typical of local anesthetic toxicity (and toxicity caused by similar substances) and generally, although not always, precede cardiac symptoms and effects. More particularly, ischemia is a restriction in blood supply or circulation, generally due to conditions in the blood vessels, hypotension, or low cardiac output, with resultant damage or dysfunction of tissue. Prolonged ischemia can also cause neurological damage. Cardiotoxicity refers to impaired automaticity and propagation of electrical impulses through the heart and its conducting system as well as damage to heart muscles and failure by the heart to adequately pump blood through the body as a result of the toxin. This can cause dangerously low blood pressure and cardiac output and therefore ischemia of important organs including the nervous system and heart. Asystole is a state of no contractions of the heart with no cardiac output or blood flow. In asystole, the heart will not typically respond to defibrillation because it is already depolarized, making resuscitation of the patient extremely difficult. Asystole is one of the conditions required for a medical practitioner to certify death. When caused by a lipophilic or amphiphilic foreign substance, these conditions can be prevented and even reversed through an infusion of a lipid emulsion of the present invention.

Preferred lipid emulsion compositions of the present invention comprise an oil, an emulsifier, a tonicity modifier, and water. In a preferred method of the invention, a patient having toxic levels of pharmaceutical drugs or other toxic substances is intravenously infused with a composition comprising the lipid emulsion wherein the toxic substance permeates the emulsion and is redistributed according to its lipid:aqueous partition coefficient onto the surface of the oil droplets and into the non-aqueous (lipid) phase of the emulsion. The lipid particles are typically several hundred nanometers in diameter and therefore a bound drug cannot pass through the endothelial gaps (approximately 4 nanometers) and is trapped in the blood stream thereby decreasing the bioavailability of the toxic substance. Such lipid sinks have wide applicability to the treatment of toxicity associated with lipophilic and amphiphilic substances. In one aspect, the invention is directed to methods for treating toxicity, particularly toxicity which results in cardiovascular and/or neurological impairment, due to foreign lipophilic and amphiphilic substances.

In some embodiments of the present invention, an infusion of a lipid emulsion composition is intravenously administered to a patient to prevent or treat the toxic effects of one or more lipophilic or amphiphilic substances already administered or ingested by the patient. As used herein, treating a patient for systemic toxicity or treating the toxic effects of a substance refers to decreasing or eliminating the adverse effects a foreign substance has on the body. The present invention has shown to be effective in treating the toxic effects of foreign lipophilic and amphiphilic substances, especially those foreign substances which cause cardiovascular impairment or neurological impairment. It is believed the present invention achieves this by absorbing the foreign substance, or its metabolites, from the bloodstream into the infused lipid emulsion, thereby reducing the bioavailability. The cardiac and neurological impairments result from elevated plasma levels of the foreign substance and therefore should predictably result in the alleviation or reversal of central nervous system toxicity by virtue of reducing the effective, or non-lipid bound, concentrations of the foreign substance. Treating a cardiovascular or neurological impairment, such as cardiotoxicity, coma or ischemia of the brain or heart, refers to decreasing, eliminating and in some cases reversing the specific adverse cardiovascular or neurological effects a foreign substance has on the body. For example, in one embodiment where a foreign toxin results in low cardiac output and ischemia of the brain or heart, administration of the lipid emulsion would remove the foreign substance from the bloodstream thereby restoring at least a portion of the cardiac output and lessening the ischemia of the brain or heart.

In some embodiments, an infusion of a lipid emulsion composition is intravenously administered to a patient prior to, shortly after, or concurrently with administration of one or more lipophilic or amphiphilic drugs, such as a pharmaceutical used in chemotherapy, for example doxorubicin (adriamycin), to the patient. In these instances, the lipid emulsion is administered to allow doses of the drug to be administered to the patient while reducing or limiting the adverse effects of that drug. With this method, greater doses of the drug can be safely administered to the patient. Preferably, the lipid emulsion composition will have little or no effect on the other drug's therapeutic effect.

In some embodiments, an infusion of a lipid emulsion composition is administered to a patient with symptoms of severe systemic toxicity in order to resuscitate or revive the patient. In particular, the lipid emulsion composition is administered to a patient experiencing or suspected of experiencing cardiovascular or neurological impairment, such as cardiotoxicity, seizures, coma, ischemia of the brain or heart, or asystole, as a result of a foreign substance. These methods are particularly useful where the patient was known to have received an anesthetic agent such as bupivacaine, mepivacaine, prilocalne, lidocaine, ropivacaine or other local anesthetics. These methods are also particularly useful in or in advance of emergency room situations where the doctor or paramedic suspects the patient of having ingested or received anti-depressants, particularly tricyclic antidepressants, beta blockers, calcium channel blockers or local anesthetics, such as cocaine.

Infusions of lipid emulsion compositions of the present invention are particularly useful to treat toxic doses of sodium channel blockers. Sodium channels are integral membrane proteins that conduct sodium ions (Na+) through a cell's plasma membrane. In one embodiment, the invention is useful in the treatment of toxic doses of lipophilic and amphiphilic sodium channel blockers such as anesthetic agents, particularly local anesthetic agents, and Class I anti-arrhythmic agents.

Most local anesthetics are amphipathic chemicals, meaning they have affinity for both lipid and water environments. This characteristic allows local anesthetics to cross plasma membrane and intracellular membranes quickly and also to interact with charged targets such as structural or catalytic proteins and signaling systems. Therefore, local anesthetics produce a variety of toxic effects in several tissue types, mainly heart, brain and skeletal muscle.

Cocaine is a local anesthetic that can induce severe cardiotoxicity. Cocaine toxicity is a serious medical problem and comprises a large fraction of drug-related emergency room visits and deaths in the United States. It has been estimated that more than 10% of the U.S. population has used cocaine at least once. Cocaine use is accompanied by a high risk of serious adverse effects involving the cardiovascular system and at high doses, cocaine toxicity resembles bupivacaine toxicity—i.e. both produce potentially fatal malignant ventricular arrhythmias, conduction block, depressed contractility, and asystole.

While the main site of both the clinically desirable and toxic effects of local anesthetics are thought to be exerted at the voltage gated sodium channel, many alternative sites have also been considered recently. Notably, the most potent, toxic local anesthetics, such as bupivacaine, interrupt practically every metabotropic and ionotropic signal transduction scheme that has been studied. Bupivacaine in particular has also been shown to disrupt each of the four components of oxidative phoshphorylation: substrate transport, electron transport, proton motive force maintenance and ATP synthesis. An interesting observation that suggests the importance of this effect in bupivacaine-induced toxicity is that the pattern of tissues affected includes those with the highest aerobic demand and least tolerance for hypoxia. Considering that local anesthetic toxicity typically presents seizures followed by cardiac arrhythmias and hypotension, this suggests a clinical picture that would be expected for a toxin that targets mitochondrial metabolism.

One embodiment of the present invention comprises materials and methods for treating toxicity associated with lipophilic and amphiphilic anesthetic agents, including but not limited to, bupivacaine, lidocaine, mepivacaine, etidocaine, amethocaine, tetracaine, procaine, 2-chloroprocaine, cocaine, prilocalne, procainamide, levobupivacaine, ropivacaine, dibucaine, other lipophilic and amphiphilic local anesthetic agents, and combinations thereof.

While the present invention is particularly useful in treating cardiotoxicity and neurological damage caused by overdoses of local anesthetics, it should be noted that experimental results indicate the present invention is also effective in treating systemic toxicity and cardiovascular impairment caused by toxic levels of other lipophilic and amphiphilic substances. Another embodiment of the present invention comprises materials and methods for treating toxicity associated with lipophilic and amphiphilic antidepressants, particularly bupropion and tricyclic antidepressants, including but not limited to imipramine, desipramine, trimipramine, clomipramine, lofepramine, amitriptyline, nortriptyline, protriptyline, dothiepin hydrochloride, doxepin, and combinations thereof.

Another embodiment of the present invention comprises materials and methods to treat toxic doses of lipophilic and amphiphilic calcium channel blockers. Calcium channel blockers are a class of drugs with effects on many cells of the body, such as the muscles of the heart, smooth muscles of blood vessels and neuron cells. The main action of many calcium channel blockers is to decrease blood pressure and so they are often prescribed to treat hypertension. Overdoses of these calcium channel blockers can result in severe cardiotoxicity, hypotension and other cardiac impairments. In one embodiment, the methods of the present invention are used to treat toxic effects of calcium channel blockers which include but are not limited to nifedipine, verapamil, and benzothiapines such as diltiazem.

Another embodiment of the present invention comprises materials and methods to treat toxic doses of lipophilic and amphiphilic beta blockers. Beta blockers are a class of drugs sometimes used for hypertension and management of cardiac arrhythmias. Accordingly, use of these beta blockers can result in severe cardiovascular impairment. In one embodiment, the methods of the present invention are used to treat toxic effects of beta blockers which include but are not limited to propranolol, metoprolol, carvedilol and bisoprolol.

A large percentage of patients needing treatment for overdoses and severe drug toxicity are emergency room visits. Unfortunately, it is often difficult to determine the substance or substances causing the toxicity and the appropriate treatment within the critical time frame. This problem is exacerbated when the patient becomes unresponsive or suffers cardiac arrest that does not respond to standard resuscitation methods. The present invention also provides a useful method for treating and resuscitating patients for severe systemic toxicity caused by one or more unknown substances in an emergency room setting.

In one embodiment, the lipid emulsion comprises between about 10 and about 40 percent oil by weight (preferably between about 10 and 30 percent), about 1 to about 5 percent emulsifier, about 1 to about 5 percent tonicity modifier, and about 60 to about 90 percent water (preferably between about 70 and 90 percent). A preferred lipid emulsion composition comprises about 20 percent by weight soybean oil, about 2 weight percent glycerin, about 1 weight percent egg yolk phospholipid, and about 77 weight percent water; however, the composition can vary depending upon the nature and lipid partition coefficient of the toxic substance in the bloodstream.

One embodiment of the present invention provides a method of treating severe systemic toxicity in a patient caused by one or more foreign substances, comprising intravenously administering a lipid emulsion composition to the patient, wherein the lipid emulsion comprises between about 10 and about 40 percent oil by weight, about 1 to about 5 percent emulsifier by weight, about 1 to about 5 percent tonicity modifier by weight, and about 58 to about 88 percent water by weight. In this embodiment, the foreign substances are lipophilic or amphiphilic substances able to be absorbed by the lipid emulsion composition in the patient's bloodstream.

In one embodiment, a lipid emulsion is first intravenously administered to a patient as an initial bolus between about 1.0 ml to about 3.0 ml per kilogram of the patient's weight. In a further embodiment, a continuous infusion is administered to a patient in the range of 0.2 ml of lipid emulsion per kilogram per minute (ml/kg/min) of the patient's weight for 2 hours, to 10 ml/kg/min for 10 minutes. In a preferred embodiment, an emulsion comprising 20 percent oil by weight is infused intravenously as an initial bolus dose of about 1.5 milliliters per kilogram over a time period of about 30-60 seconds followed by a steady-state rate of about 0.25 milliliters per kilogram per minute for a time period of about 30-60 minutes. In this embodiment, the bolus dose can be repeated up to twice if the patient's condition does not improve, and the steady-state infusion rate can be increased to 0.5 milliliters per minute if the blood pressure begins to decline.

Other lipid-emulsions according to the present invention include emulsions comprising one or more of the following substances: glycerophospholipids such as phosphatidylcholine; cholesterol; stearylamine; phosphatidylserine; phosphotidylglycerol and other lipids. Also included within the scope of the invention are microemulsions which include oil, water, and an amphiphile system that is macroscopically monophasic, optically isotropic, thermodynamically stable and characterized by ultra-low interfacial tension values.

The invention is also directed to kits for the convenient administration of lipid emulsions of the present invention to a patient. The kit is also useful for administering other therapeutic substances, such as chemotherapy drugs, by way of a regimen comprising the administration of a bolus of the lipid emulsion with, or shortly before or after, the infusion of the therapeutic agent over a period of time.

DETAILED DESCRIPTION OF THE INVENTION

Figure 1:
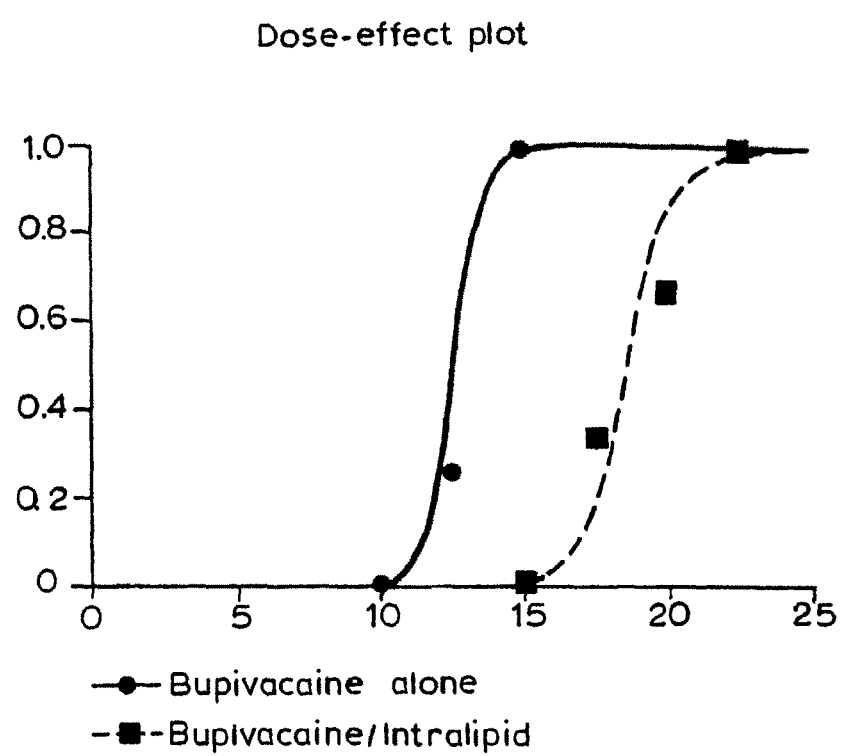
FIG. 1 is a graph depicting the analysis of the mortality fraction versus the bupivacaine dose for animals treated according to protocol 2 (lipid resuscitation) for intravenous infusions of either saline or a lipid emulsion composition.

The present invention relates to lipid emulsion compositions and to methods and apparatus for reducing the bioavailability and toxicity of foreign substances present in the circulation by intravenous administration of the lipid emulsion. A preferred method for the treatment of systemic toxicity includes making a patient in need of such therapy rapidly lipemic by the intravenous infusion of an initial large bolus dose of an emulsion followed by a slower, steady-state rate of infusion of the emulsion. Although the rate of infusion can vary with respect to the particular emulsion utilized with the toxic agent involved and with the particular patient, by way of example, an initial rate of the infusion may be in the range of about 1.5 ml/kg, over a time period of about 30-60 seconds, followed by a steady-state rate in the range of about 0.25 ml/kg/min to about 0.5 ml/kg/min for a time period of about 30 minutes.

The lipid emulsion composition of the present invention comprises an oil, an emulsifier, a tonicity modifier, and water. Additional ingredients can include a surfactant, a co-solvent, a bacteriostat, a preservative, a biologically active ingredient, and an adsorbent.

Preferably the oil in the emulsion composition is one or more oils selected from the group consisting of monoglycerides, diglycerides, triglycerides, and mixtures thereof. Any oil that is can be intravenously administered to a patient without eliciting toxic side effects may be suitable for the present invention. Preferably, the oil is a naturally occurring plant or animal oil that can be absorbed and metabolized by the human body. For example, vegetable oils and fish oils have been previously successfully administered to patients intravenously for nutritional purposes, and would be suitable for use in the present invention. More preferably, the oil is a naturally occurring plant oil selected from the group consisting of soybean oil, cottonseed oil, safflower oil, corn oil, coconut oil, sesame oil, peanut oil, olive oil, and mixtures thereof. Most preferably the oil is soybean oil. In addition, the oil can be an animal oil or a fish oil such as cod liver oil. The oil can also can be a mineral oil or a chemically-synthesized oil such as 2-linoleoyl-1,3-dioctanoyl glycerol. Semisynthetic mono-, di- or triglycerides, and mixtures thereof, may also be used and include Medialipid™ (a mixed medium and long-chain triglyceride emulsion from B. Braun Melsunsen AG, Germany), rac-glyceryl-1-monopalmitic, acyl glyceryl-1-monoolein, 1,2-dipalmitic, 1,3-dipalmitic, trimyristin, tripalmitin, tristearin, triolein, trilaiden and the like.

The emulsifier in the lipid emulsion composition preferably is a naturally-occurring phospholipid. Preferred phospholipids useful in the present invention are derived from egg or soy sources. Exemplary phospholipids include but are not limited to, egg yolk phospholipids, hydrogenated egg yolk phospholipids, soybean phospholipids, hydrogenated soybean phospholipids, and mixtures thereof. Preferably, the phospholipid is egg yolk phospholipid. The emulsifier also can be a synthetic lecithin such as dihexanoyl-L-α-lecithin. Among the other emulsifiers useful in the practice of the present invention are other glycerophospholipids such as phosphatidylcholine, cholesterol, stearylamine, phosphatidylserine, phosphatidylglycerol and other lipids.

The tonicity modifier preferably is a member of the group consisting of glycerin, sorbital, polyoxyethylated hydrocarbons, and $C_6$-$C_{20}$ saturated or unsaturated aliphatic acids. The optional co-solvent preferably is an alcohol such as isopropanol or benzyl alcohol or the like. The bacteriostat or preservative can be any of those commercially available which are non-toxic. The biologically active ingredient can be a desired drug or reactant which can render the toxic agent non-toxic or which may act to counter the physiological effects of the toxic agent, while the adsorbent can be, for example, charcoal, silica gel, or the like.

In formulating the emulsion, the oil is preferably present in the range of about 10 to about 30 percent by weight of the composition, more preferably between about 20 and 30 percent, and more preferably approximately 30 percent. The emulsifier in the composition is preferably present in an amount in the range of about 1 to about 5 percent by weight of the composition. The tonicity modifier in the composition is preferably present in an amount in the range of about 1 to about 5 percent by weight of the composition. Water is preferably present in the range of about 68 to about 88 percent by weight.

A preferred lipid emulsion composition comprises about 20 percent (by weight) soybean oil, about 2 percent (by weight) glycerin, about 1 percent (by weight) egg yolk phospholipid, and about 77 percent (by weight) water. Another embodiment comprises about 30 percent (by weight) soybean oil, about 2 percent (by weight) glycerin, about 1 percent (by weight) egg yolk phospholipid, and about 67 percent (by weight) water. Yet, another embodiment comprises about 10 percent (by weight) soybean oil, about 2 percent (by weight) glycerin, about 1 percent (by weight) egg yolk phospholipid, and about 87 percent (by weight) water. Although certain specific lipid emulsions are hereby exemplified, it is understood that other lipid emulsions that fall within the prescribed ranges are also encompassed by the present invention, for example, lipid emulsions comprising 15 percent and 25 percent soybean oil are also suitable.

In another embodiment, the lipid emulsion composition comprises about 20 percent (by weight) corn oil or cottonseed oil, about 2 percent (by weight) glycerin, about 1 percent (by weight) egg yolk phospholipid or any other naturally-occurring phospholipid, and about 77 percent (by weight) water. In another embodiment, the lipid emulsion composition comprises about 20 percent (by weight) cod liver oil, about 2 percent (by weight) glycerin, about 1 percent (by weight) egg yolk phospholipid or any other naturally-occurring phospholipid, and about 77 percent (by weight) water. Although certain specific lipid emulsions are hereby exemplified, it is understood that lipid emulsions comprising other oils described herein are also encompassed by the present invention, for example, lipid emulsions comprising any of the naturally occurring vegetable or animal oils are suitable.

The methods of the present invention can be used to treat the toxic effects of lipophilic and amphiphilic substances circulating in the bloodstream. Lipophobic substances are not likely to interact with the lipid emulsion and thus the bioavailability is unlikely to be affected by an intravenous infusion of the lipid emulsion composition. Preferably, substances with greater organic to aqueous partition coefficients are more amendable to lipid infusion therapy for treatment. For example, Table 1 shows octanol:water partition coefficients for a list of drugs with toxic effects. Those with a log partition coefficient of 2 or greater should be particularly amenable to the methods of the present invention for the treatment of toxicity. As shown in Table 1, lamotrigine, although a suspected $Na^+$ channel blocker, would not likely be a good candidate for treatment with lipid infusion therapy due to its low lipophilic characteristics. In general, drugs with low lipophilic values have a log partition coefficient<0, drugs with medium lipophilic values have a log partition coefficient between 0-3, substances with high lipophilic values have a log partition coefficient between 3-4, and substances with very high lipophilic values have a log partition coefficient between 4-7.

TABLE 1 logP values from Wilson and Gisvold's Textbook of Organic Medicinal and Pharmaceutical Chemistry:

| | |
|---|---|
| bupivacaine | 3.64 |
| bupropion | 3.47 |
| clomipramine | 5.19 |
| desipramine | 3.97 |
| dibucaine | 4.40 |
| diltiazem | 4.53 |
| imipramine | 4.46 |
| lamotrigine | −0.19 |
| lidocaine | 2.36 |
| mepivacaine | 2.04 |
| nifedipine | 3.05 |
| nortriptyline | 5.65 |
| propranolol | 3.10 |
| ropivacaine | 3.11 |
| tetracaine | 3.49 |
| verapamil | 4.91 |

P = partition coefficient = [organic]/[aqueous]
logP = log10 P (eg, logP = 1 means a 10:1 organic:aqueous coefficient; logP = 0 means a 1:1 ratio; and logP = −1 is a 1:10 ratio, etc)

In the following examples, the commercially available lipid emulsion composition, Intralipid® was used. Intralipid® (Baxter) was introduced into the U.S. marketplace in 1975 for intravenous use. Intralipid® contains 10%-30% w/v soybean oil as a source of polyunsaturated fatty acids, and 1.2% w/v of purified egg phospholipids which act as an emulsifying agent. The remainder of the composition is water added to achieve final lipid concentration in the range of about 10% w/v to about 30% w/v as is desired. Glycerol is added to make the lipid emulsion isotonic, with about 2.25% w/v present in Intralipid®. The pH range of the Intralipid® emulsion is from about 5.5 to 8.

The lipid emulsion can be prepared by any convenient means, such as sonication and the like. The components of the emulsion can be mixed or premixed in any order prior to the sonication or other preparation process. The emulsion preferably comprises particles in the range of about 0.25 microns to about 0.75 microns in diameter.

While the invention is exemplified by way of reducing or eliminating the toxic effects of local anesthetic agent overdoses, such as bupivacaine, it is readily apparent to one of skill in the art that the methods of the present invention may also be used to treat toxicity associated with other lipophilic or amphiphilic agents including other sodium channel blockers, other anesthetic agents such as cocaine, tetracaine and etidocaine, tricyclic antidepressants (e.g., amitryptiline), adriamycin, organic solvents, alcohol, and class I antiarrhythmic agents. Other exemplary lipophilic toxic agents which may be sequestered using the emulsions of the present invention include gasoline, inhaled propellants, N,N-diethyl-m-toluamide (DEET) or any of the agents in the above list having a logP octanol:water partition coefficient greater than 1.

The methods and compositions of the present invention are applicable to several clinical scenarios in addition to treatment of acute toxicity such as is exemplified below. For example, in the situation where a patient will be receiving a known amount of an agent with potentially serious side effects (e.g., a lipophilic chemotherapeutic agent such as adriamycin), an emulsion according to the invention may be administered to the patient to reduce toxicity of the agent thereby increasing its safe dose. In this embodiment, the lipid emulsion can be administered concurrently with the agent, or shortly before or after the agent is administered.

In another scenario, when an acutely ill patient presents with apparent toxicity or a possible overdose of a known or unknown drug, e.g., presenting with cardiac arrhythmias in a young, otherwise healthy person, or a person with a history of depression being treated with tricyclic antidepressants, the patient may be treated with a lipid emulsion according to the present invention.

The amount of toxin might be known precisely, or entirely unknown. In the latter case, the patient's clinical status (mildly or severely ill) will guide treatment. The length of treatment following an initial dose will be determined by clinical response against a predetermined maximum safe dose for a patient's weight, which is readily determined by routine methods. The spent emulsion will be metabolized slowly (over hours) by the patient's body, for example by lipoprotein lipase which releases the fatty acids from the triglycerides. The toxin is then released from the emulsion droplets, but this slow release allows the patient's normal metabolism to chemically modify, excrete, or otherwise detoxify the toxin. The emulsion can be delivered via any peripheral or central vein.

The invention is described in more detail below by way of non-limiting examples. Example 1 describes the pretreatment of animals with a lipid emulsion and the effect of shifting the dose-response to bupivacaine induced asystole. Example 2 demonstrates the resuscitation of an animal from a toxic dose of bupivacaine by use of an intravenously infused lipid emulsion. Example 3 demonstrates the resuscitation of an animal from a toxic dose of cocaine. Examples 4 and 5 describe delivery devices and kits for the administration of a lipid emulsion to a patient.

EXAMPLE 1

Pretreatment with a Lipid Emulsion Composition Shifts the Dose-Response to Bupivacaine Induced Asystole in Rats Studies were undertaken to assess the ability of a lipid emulsion to shift the dose-response to drug-induced asystole (heart stoppage) in rats. Pretreatment with a lipid emulsion increased the dose of bupivacaine (a local anesthetic) required to induce asystole. Racemic bupivacaine hydrochloride was purchased from Sigma (St. Louis, Mo.) while tritiated bupivacaine was purchased from Moravek Biochemicals (Brea, Calif.). Intralipid® was purchased from Baxter Healthcare (Deerfield, Ill.). Male Sprague-Dawley rats weighing between about 250 grams to about 370 grams were used in all experiments.

Animals were first anesthetized in a bell jar with isoflurane to allow intubation, then mechanically ventilated with about 1.75% isoflurane in about 100% oxygen using a Harvard rodent ventilatory model 680 in conjunction with a tidal volume of 3 ml and a starting rate of about 40 breaths per minute. Catheters were inserted into the right internal jugular vein, the right carotid artery, and the right internal iliac vein. Electrocardiogram (BCG) was monitored via three subcutaneous needle electrodes in each rat. Arterial blood gas measurements were made after the induction of general anesthesia and again just prior to infusions to confirm a $pCO_2$ in the range of about 30 to about 35 mm Hg and a pH in the range of about 7.35 to about 7.45 units.

All animals were allowed to stabilize for about 15 minutes while arterial blood pressure and ECG were monitored. There were six animals in each group. Control animals (group 1) received saline intravenously as pretreatment while test animals (groups 2-4) were pretreated intravenously with the lipid emulsion composition Intralipid® at concentrations of either about 10% by weight (group 2), about 20% by weight (group 3), or about 30% by weight (group 4) in saline. All pretreatments were infused at a rate of about 3 ml/kg/min for 5 minutes via the internal jugular vein.

Immediately following pretreatment, all animals received an infusion of about 0.75% bupivacaine via the internal iliac catheter at a rate of about 10 mg/kg/min to an end point of about ten seconds of asystole. Blood was then drawn from the aorta into a heparinized syringe for plasma bupivacaine determinations. The cumulative lethal dose of bupivacaine was calculated in mg/kg for all animals.

Plasma bupivacaine concentrations were determined by high performance liquid chromatograph (HPLC) after the samples had been extracted with hexane. The method of hexane extraction was validated with bupivacaine spiked samples and provided greater than about 95% recovery of bupivacaine from both normal and lipemic plasma. Thus, plasma bupivacaine concentrations reflected total bupivacaine content in both the aqueous and lipid phases of the specimen. The compounds were separated using a C18 column, 5 micrometer, 150 by 3.9 mm internal diameter (Symmetry, Waters Associates, Milford, Mass.) using the anaesthetic mepivacaine as an internal standard. The mobile phase consisted of about 25% acetonitrile in about 25 mM phosphate buffer adjusted to about pH 3.0. The flow rate was about 1 ml/min with a constant column temperature of about 30° C. The retention time for the mepivacaine internal standard was about 1.8 min. and about 4.0 min for bupivacaine during a 6 min. long run. The drugs were detected at a wavelength of about 215 nm.

The bupivacaine lipid:aqueous partition coefficient was determined for a mixture of Intralipid® and rat plasma. Blood obtained from rats by direct heart puncture under halothane anesthesia was centrifuged and the plasma was separated. Equal volumes of about 30% Intralipid® and plasma (approximately 2 ml each) were combined and vortexed. Approximately 1.0 µCi of titriated bupivacaine (specific activity 0.81 Ci/mole) was added to the mixture to a final bupivacaine concentration of about 93 µg/ml. This mixture was vortexed again then separated into aliquots of about 1 ml. These aliquots were allowed to sit undisturbed for about one hour at about 38° C., then centrifuged at about 10,000 g for about 10 minutes. High speed centrifugation separated each of these mixtures into a clear aqueous phase (about 0.85 ml) under a lipid phase (about 0.15 ml). The latter comprised a clear layer beneath a very thin white cap. The cap was removed then redissolved in saline to a total volume of about 1 ml. Aliquots of this solution and the aqueous plasma phase were then analyzed for tritiated bupivacaine content by liquid scintillation counting. The bupivacaine lipid:aqueous partition coefficient was given by the ratio of bupivacaine in the combined lipid phase (following correction for saline dilution) to the bupivacaine in the aqueous phase. This experiment was performed in triplicate.

Bupivacaine dose and plasma concentrations were analyzed by Kruskal-Wallis one way analysis of variance on ranks. Post hoc testing of both data sets was performed by Student-Newman-Keul's method for multiple comparisons (SigmaStat, Jandel Scientific/San Rafael, Calif.). Cumulative bupivacaine dose data were nonparametric and median values were compared by differences of ranks. Plasma bupivacaine concentration data were parametric and differences in mean values were evaluated. Probit analysis (CalcuSyn, Biosoft/Cambridge, England) was used to compare bupivacaine $LD_{50}$ values in the saline and lipid portions. The difference in survival of the two groups at 15 mg/kg bupivacaine was further evaluated using a z test of proportions. Statistical significance in all experiments was taken as p less than or equal to 0.05. A dose-effect plot comparing bupivacaine alone with bupivacaine and Intralipid® is shown in FIG. 1.

The results indicate that the lethal bupivacaine dose among all animals ranged from about 12.7 mg/kg in an animal receiving saline pretreatment to about 111 mg/kg in an animal receiving an emulsion composition containing about 30% Intralipid®. Median bupivacaine lethal doses were as follows: (mg/kg; 25th percentile-75th percentile): Group 1 (saline) 17.8, 13.2-20.3; Group 2 (10% Intralipid®) 27.6, 22.2-31.7; Group 3 (20% Intralipid®) 49.8, 41.2-57.8; Group 4 (30% Intralipid®) 82.0, 71-3-101. Statistical significance for differences in median lethal bupivacaine does was achieved between all groups (p less than 0.001).

The mean plasma bupivacaine concentrations at the time of asystole for protocol 1 were (mcg/ml+/−standard error of the mean): group 1, 93.3+/−7.6; group 2, 115+/−15; group 3,177+/−31; and group 4, 212+/−45. Statistical significance was achieved for the difference in mean concentrations between groups 1 and 4.

Probit analysis of the data from protocol provided the following bupivacaine $LD_{50}$ values for the two treatment groups [lower and upper 95% confidence intervals (mg/kg): saline, 12.5, 11.8-13-4; lipid, 18.5, 17.8-19.3]. A z test of proportions at 15 mg/kg bupivacaine showed significance in the difference in survival between the two groups at this dose (p less than 0.004). The lipid:aqueous ratio of bupivacaine concentrations (+/−standard error) was 11.9+/−1.77. When equal volumes of a solution of about 30% by weight Intralipid® and plasma were combined, the actual lipid volume was about 15% of total, and the percent of total bupivacaine dissolved in the lipid phase of this mixture (+/standard error) was about 75.3%+/−1.32%.

EXAMPLE 2

Resuscitation from a Toxic Dose of Bupivacaine with a Lipid Emulsion Composition Experiments were performed to evaluate the ability of a lipid emulsion to resuscitate an animal from a toxic dose of bupivacaine. All animals were anaesthetized, instrumented and stabilized at about 1.75% isoflurane as described in Example 1, and arterial blood pressure and ECG were continuously monitored. Each rat received an intravenous dose of bupivacaine (see below for doses) for more than about 10 seconds by Harvard infusion pump, via the iliac catheter. Immediately after the bupivacaine dose, isoflurane was stopped and mechanical ventilation was continued with about 100% oxygen, with all animals receiving an infusion of either saline or about 30% by wt. solution of Intralipid® via the internal jugular catheter. In each case, the initial infusion rate was about 7.5 ml/kg bolus over 30 seconds, followed by a steady-state rate of about 3 ml/kg/min for about 2 minutes. Chest compressions were given during infusion for any animal experiencing more than about 15 seconds of asystole. Survival was scored about 5 minutes after the bupivacaine bolus and required both heart rate greater than about 100 beats per minute and systolic blood pressure greater than about 60 mmHg. Isoflurane at a concentration of about 1.75% was restarted whenever the blood pressure or heart rate met the survival criteria. Thus, a difference in survival between control and treated animals required rapid reversal of the cardiotoxic effects of a potentially fatal bupivacaine dose.

Preliminary experiments with this protocol established the bupivacaine bolus dose ranges necessary to achieve groups with 100% survival, 100% mortality and at least one intervening dose for both control and lipid treatment. These were mg/kg, 12.5 mg/kg, and 15 mg/kg for the controls and 15 mg/kg, 17.5 mg/kg, 20 mg/kg and 22.5 mg/kg for lipid treated animals.

This resuscitation protocol provided a stringent test of efficacy of the lipid emulsion composition in treating bupivacaine induced cardiovascular collapse. The short fixed injection interval (10 seconds) modeled the clinical occurrence of a rapid intravascular bupivacaine injection. The experimental results showed about 48% increase in the bupivacaine $LD_{50}$ when resuscitation included lipid infusion (from about 12.5 mg/kg to 18.5 mg/kg). At 15 mg/kg, a usually fatal bupivacaine dose, the lipid infused animals survived.

As illustrated by the foregoing results, lipid infusion reduces bupivacaine-associated cardiotoxicity. Partition experiments suggest that the primary benefit of lipid infusion results from a lipid sink effect where the poison is drawn from the blood into the non-aqueous component of the emulsion thereby reducing the amount of toxin in the cells such that toxicity is reversed. Other mechanisms may also be active. These observations suggest that the use of intravenously infused lipid emulsions can reverse toxic effects, particularly the cardiotoxic effects of lipophilic or ampiphilic agents. An important parameter in the design of such emulsion compositions is the partition coefficient of the toxic agent in the emulsion which can be readily determined by methods such as those described above.

EXAMPLE 3

Figure 3:
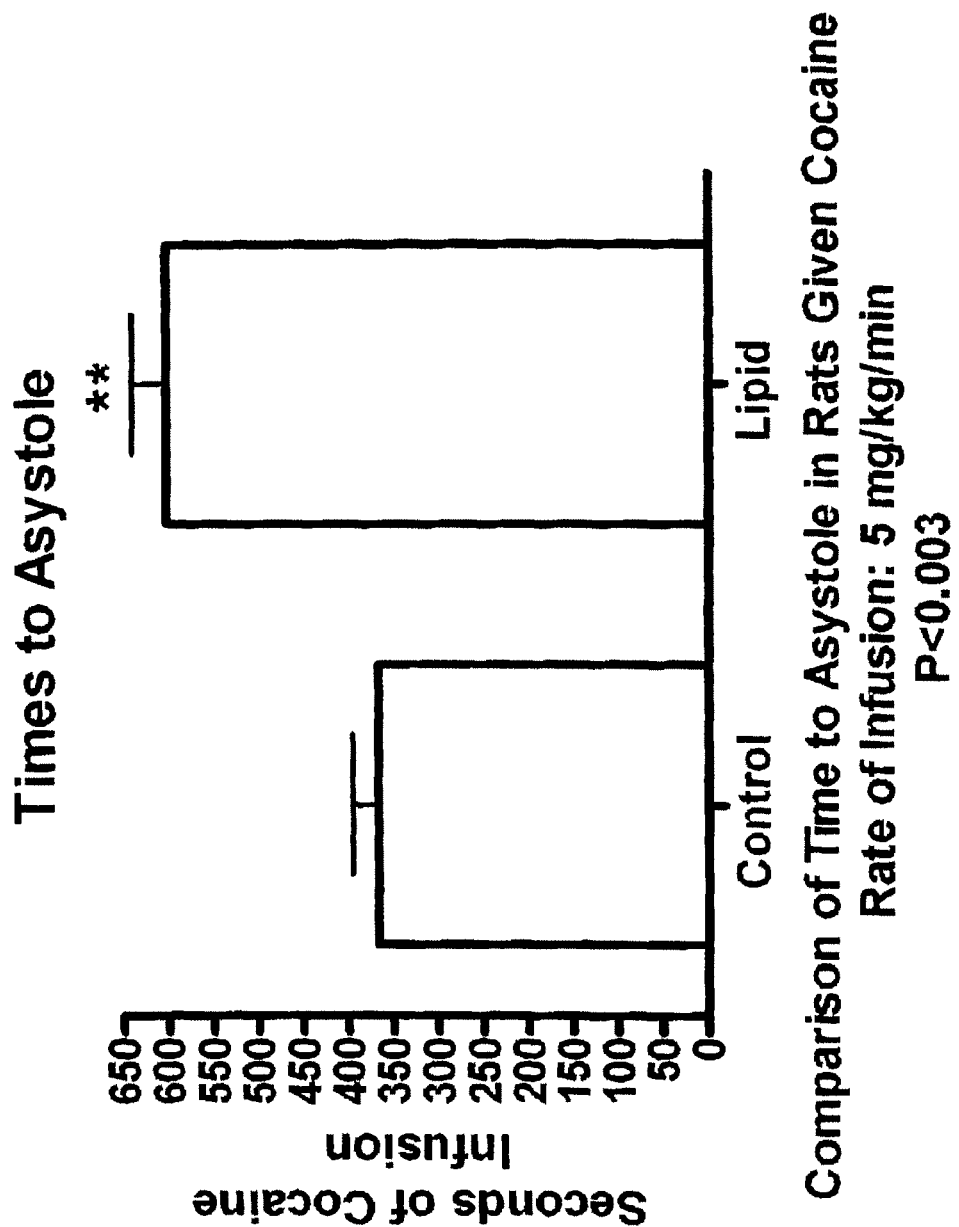
FIG. 3 is a comparison of time to asystole in rats given cocaine and rats given cocaine after an infusion of a lipid emulsion of the present invention. Rate of infusion is 5 mg/kg/min, P<0.003.
Figure 4:
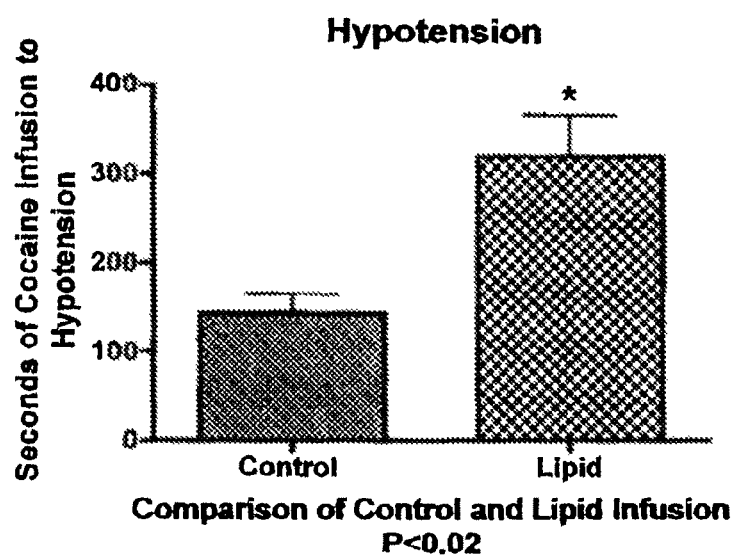
FIG. 4 is a comparison of time to hypotension in rats given cocaine and rats given cocaine after an infusion of a lipid emulsion of the present emulsion. P<0.02.

Effect of Pretreatment with a Lipid Emulsion Composition on Cocaine Toxicity in Rats Because of the significant potential benefit, experiments were performed to test an infusion of a lipid emulsion as a method of treating cocaine toxicity. Anesthetized, ventilated rats were infused with a lipid emulsion (20% Intralipid® at 10 ml/kg for 2 minutes) and then administered an intravenous infusion of cocaine at 5 mg/kg/min to hypotension (blood pressure is less than 40 mmHg) or asystole (no heartbeat for 5 seconds). As illustrated in FIG. 4, mean times to 40 mmHg were 143±22 seconds and 320±46 seconds for control (saline) and lipid treated animals, respectively (n=8, for both groups). For asystole, as shown in FIG. 3, the times were 368±27 seconds and 602±38 seconds for control and lipid-treated rats, respectively. Unpaired t-test with Welch's correction showed that these differences were significant for both the hypotension ($p<0.02$) and asystole ($p<0.003$) endpoints. Thus, pretreatment with a lipid emulsion composition shifts the dose-response of cocaine in much the same way as bupivacaine. This is an expected result given the similar properties and effects between cocaine and bupivacaine. These findings indicate that lipid infusion can be used to treat patients experiencing acute cardiovascular compromise in cocaine overdose.

EXAMPLE 4

Emulsion Delivery Device

Figure 2:
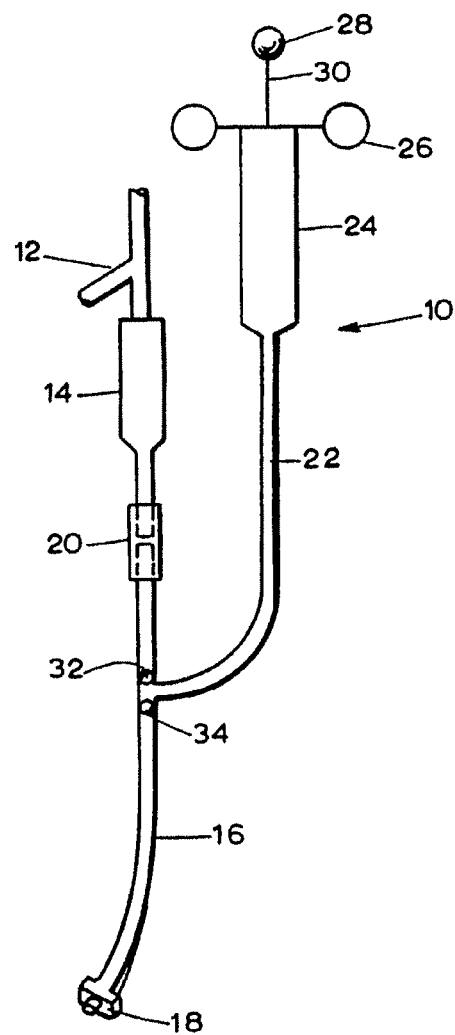
FIG. 2 depicts a device for administering to a patient the emulsions of the present invention.

A delivery device 10 constructed in accordance with the teachings of the invention is illustrated in FIG. 2. As shown in that figure, the delivery device 10 includes a vented spike 12 for insertion into a lipid emulsion-containing bottle or other suitable container (not shown) suspended from an IV pole in a conventional manner. The vented spike 12 is in communication with a drip chamber 14 which is, in turn, in communication with a main delivery channel implemented by a length of tubing 16 which preferably has a large bore. The bottom end of the tubing 16 is provided with a connecting means, which preferably is a conventional luer lock 18. To control the flow of fluid from the drip chamber 14, the delivery device 10 is provided with a conventional roller clamp 20 but other means for regulating fluid flow are also contemplated. The roller clamp 20 operatively engages the outer surface of the tubing 16 immediately below the drip chamber 14. By adjusting the roller clamp 18, health care personnel can regulate the rate at which fluid exits the drip chamber 14.

In accordance with one aspect of the invention, the delivery device is provided with a length of extension tubing 22. As shown in FIG. 2, one end of the extension tubing 22 is in fluid communication with the large bore tubing 16. The extension tubing 22 may be integrally formed with or otherwise connected with the large bore tubing 16. The opposite end of the extension tube 22 is coupled to a syringe 24. The syringe 24 is preferably implemented with one or more finger rings 26 and a thumb ring 28 on its piston 30. Significantly, the syringe 24 can be suspended from the IV pole by its thumb ring 28. Suspending the syringe 24 in this manner prevents the extension tubing 22 and the syringe 24 from kinking when the injection fluid (emulsion) is just dripping and not being pushed from the syringe 24 via the piston 30.

For the purpose of controlling the direction of fluid flow through the device 10, the delivery device is provided with two one-way valves 32 and 34. Preferably ball valves are utilized in the invention. As shown in FIG. 2, a first one of the ball valves 32 is located above the junction of the large bore tubing 16 and the extension tube 22. This ball valve 32 prevents fluid flowing through the extension tube 22 from backing up the large bore tubing 16 towards the drip chamber 14. The second ball valve 32 is located below the junction of the large bore tubing 16 and the extension tube 22. This second ball valve 34 prevents fluid from passing back up the main delivery channel towards the syringe 24.

Preferably, the thumb ring 28 of the syringe 24 is suspended from the IV pole at substantially the same height as the top of the lipid emulsion bottle. As a result, the length of the extension tubing 22 is preferably defined by the distance from the ball valve 32 to the IV pole. This distance is, in turn, defined by the length of the tubing 16 from the vented spike 12 to the ball valve 32 and the length of the lipid emulsion bottle. Preferably, the length of the extension tubing 22 is selectively within these parameters to avoid any kinking when the syringe 24 is suspended from the IV pole.

While the above-described delivery device is particularly useful for administering the emulsions of the present invention, it is readily apparent that it may also be used to administer therapeutic or prophylactic substances separately or in conjunction with the lipid emulsion.

EXAMPLE 5

Pre-packaged Kits for the Administration of Lipid Emulsions to a Patient for Treating Toxicity Pre-packaged kits can be used to provide quick administration of an effective dose of a lipid emulsion to a patient experiencing systemic shock, especially those experiencing life threatening cardiovascular impairment. These kits would be particularly useful in emergency room type settings. Such kits would have to be lightweight, compact and easily accessible.

One such kit comprises a lightweight container having a pre-filled sterile syringe suitable for intravenously injecting the contents of the syringe directly into a patient. The syringe contains a lipid emulsion composition of the present invention, allowing the lipid emulsion to be immediately injected into the patient once removed from the container. Alternatively, the kit contains the lipid emulsion composition in a sealed sterile medical bag, approximately 500 ml in volume, fluidly connected to IV tubing that has a needle or cannulae at the end. By fluidly connected, it meant that fluid in the medical bag can flow through the IV tubing and through the needle or cannulae at the end. Thus, rather than inject the lipid emulsion into the patient with a syringe, the lipid emulsion is delivered via a more conventional IV drip. In either embodiment, the kit also contains printed instructions for the administration of the lipid emulsion composition for the treatment of severe systemic shock. In another embodiment, the kit contains both a syringe and a medical bag so that the initial bolus is delivered by the syringe and is followed by a continuous infusion of the lipid emulsion from the bag. The syringe is attached by a luer to a one-way valve so that additional boluses could be given. The syringe then hangs from the IV pole when not in use.

The lipid emulsion in the kit preferably comprises between about 10 and about 30 percent oil by weight, about 1 to about 5 percent emulsifier by weight, about 1 to about 5 percent tonicity modifier by weight, and about 68 to about 88 percent water by weight. More preferably the kit contains a lipid emulsion composition comprising about 20 percent vegetable oil by weight, about 2 percent glycerin by weight, about 1 percent egg yolk phospholipid by weight, and about 77 weight percent water.

Optionally, the kit also contains a nomogram showing the preferred dose of the lipid emulsion composition to be administered to the patient according to weight of the patient. The nomogram should be prominently displayed, such as either on the container, the medical bag or the syringe itself, to make it easy to determine what the appropriate dose for the patient in any given situation.

EXAMPLE 6

Emergency Resuscitation

To treat a patient experiencing systemic toxicity who does not respond to standard resuscitative protocols, including CPR, and who is known or suspected to have ingested a lipophilic or amphiphilic foreign substance that causes systemic toxicity, the patient is first infused with an initial bolus of a lipid emulsion composition. The initial bolus should be approximately 1.5 ml of the lipid emulsion composition per kilogram of the patient's weight. The lipid emulsion preferably comprises about 20 percent animal or vegetable oil by weight, about 1 to about 5 percent glycerin by weight, about 1 to about 5 percent egg yolk phospholipid by weight, and about 77 percent water by weight.

The initial bolus is followed by continuous infusions of the lipid emulsion composition. The rate and duration of the continuous infusion can vary depending on the patient's status. The continuous infusion can range from 0.2 ml of lipid emulsion per kilogram per minute (ml/kg/min) of the patient's weight for 2 hours, to 10 ml/kg/min for 10 minutes. Preferably, the continuous lipid emulsion composition is administered at a rate of 0.25 ml/kg/min for 30 to 60 minutes, or until cardiovascular stability is re-established. Further administration of a 1.5 ml/kg bolus is performed 1-2 times for persistent asystole.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

One of ordinary skill in the art will appreciate that starting materials, reagents, materials, device elements, analytical methods, assay methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

While certain specific examples of chemical classes have been specified, it would be obvious to one skilled in the art that other specific compounds of the same class having similar structures and effects would also be expected to be treatable by the present invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of analysis, additional biological materials, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

We claim:

1. A method of treating cardiovascular impairment in a patient caused by one or more foreign substances already administered to or ingested by the patient, said method comprising:

intravenously administering a lipid emulsion composition to the patient wherein said lipid emulsion comprises between about 10 and about 40 percent oil by weight, about 1 to about 5 percent emulsifier by weight, about 1 to about 5 percent tonicity modifier by weight, and about 58 to about 88 percent water by weight, wherein said one or more foreign substances are lipophilic or amphiphilic substances able to be absorbed by the lipid emulsion composition in the patient's bloodstream, and wherein said one or more foreign substances are selected from the group consisting of bupivacaine, lidocaine, mepivacaine, etidocaine, amethocaine, tetracaine, procaine, 2-chloroprocaine, cocaine, prilocaine, procainamide, levobupivacaine, ropivacaine, dibucaine, and combinations thereof.

2. The method of claim 1 wherein said one or more foreign substances comprises cocaine.

3. The method of claim 1 wherein the oil is a naturally occurring vegetable or animal oil.

4. The method of claim 1 wherein the oil is selected from the group consisting of soybean oil, cottonseed oil, safflower oil, corn oil, coconut oil, sesame oil, peanut oil, olive oil, cod liver oil and mixtures thereof.

5. The method of claim 1 wherein the oil is soybean oil.

6. The method of claim 1 wherein the lipid emulsion composition comprises between about 10 and about 30 percent oil by weight, about 1 to about 5 percent emulsifier by weight, about 1 to about 5 percent tonicity modifier by weight, and about 68 to about 88 percent water by weight.

7. The method of claim 1 wherein said lipid emulsion composition is administered at a steady rate of about 0.25 ml to about 0.5 ml per kilogram of the patient's weight per minute for a time period of about 30 minutes to about 60 minutes.

8. The method of claim 1 wherein an initial bolus of the lipid emulsion composition between about 1.0 ml to about 3.0 ml per kilogram of the patient's weight is administered to the patient for a period of about 30 seconds to about 60 seconds.

9. The method of claim 1 wherein the patient receiving the lipid emulsion composition is in asystole.

\* \* \* \* \*